United States Patent
Wigbers et al.

(10) Patent No.: US 8,933,223 B2
(45) Date of Patent: *Jan. 13, 2015

(54) PROCESS FOR PREPARING A CYCLIC TERTIARY AMINE

(75) Inventors: Christof Wilhelm Wigbers, Mannheim (DE); Johann-Peter Melder, Böhl-Iggelheim (DE); Bernd Stein, Alsbach-Hähnlein (DE); Harald Meiβner, Hassloch (DE)

(73) Assignee: BASF SE, Ludwigshafen (DE)

(*) Notice: Subject to any disclaimer, the term of this patent is extended or adjusted under 35 U.S.C. 154(b) by 0 days.

This patent is subject to a terminal disclaimer.

(21) Appl. No.: 13/273,784

(22) Filed: Oct. 14, 2011

(65) Prior Publication Data

US 2012/0095221 A1   Apr. 19, 2012

Related U.S. Application Data

(60) Provisional application No. 61/392,960, filed on Oct. 14, 2010.

(51) Int. Cl.
*C07D 295/02* (2006.01)
*C07D 295/00* (2006.01)
*C07D 295/03* (2006.01)
*C07D 295/023* (2006.01)

(52) U.S. Cl.
CPC .......... *C07D 295/03* (2013.01); *C07D 295/023* (2013.01)
USPC ............ 544/178; 544/404; 546/184; 548/579

(58) Field of Classification Search
CPC .......................... C07D 295/023; C07D 295/03
See application file for complete search history.

(56) References Cited

U.S. PATENT DOCUMENTS

| | | |
|---|---|---|
| 3,166,558 A | 1/1965 | Mascioli |
| 3,275,554 A | 9/1966 | Wagenaar |
| 3,751,475 A | 8/1973 | van der Voort et al. |
| 3,997,368 A | 12/1976 | Petroff et al. |
| 4,014,933 A | 3/1977 | Boettger et al. |
| 4,323,550 A | 4/1982 | Goupil |
| 4,442,306 A | 4/1984 | Mueller et al. |
| 4,739,051 A | 4/1988 | Schroeder et al. |
| 4,832,702 A | 5/1989 | Kummer et al. |
| 4,845,218 A | 7/1989 | Schroeder |
| 4,851,578 A | 7/1989 | Fischer et al. |
| 4,851,580 A | 7/1989 | Mueller et al. |
| 4,910,304 A | 3/1990 | Fischer et al. |
| 5,002,922 A | 3/1991 | Irgang et al. |
| 5,110,928 A | 5/1992 | Schroeder et al. |
| 5,463,130 A | 10/1995 | Witzel et al. |
| 5,530,127 A | 6/1996 | Reif et al. |

(Continued)

FOREIGN PATENT DOCUMENTS

| | | |
|---|---|---|
| CA | 1046166 A1 | 1/1979 |
| CA | 1055677 A1 | 6/1979 |

(Continued)

OTHER PUBLICATIONS

Clark, Jim. "Introducing Alcohols." Copyright 2003. Available at: < http://www.chemguide.co.uk/organicprops/alcohols/background.html >.*
Wikipedia. "Alkane." Published on Web: Dec. 20, 2008. Available at: < http://web.archive.org/web/20081220105723/http://en.wikipedia.org/wiki/Alkane >.*
International Search Report for PCT/EP2011/067612 dated Nov. 22, 2011.
U.S. Appl. No. 13/910,602, filed Dec. 2013.
U.S. Appl. No. 13/906,931, filed Dec. 2013.
U.S. Appl. No. 13/906,960, filed Dec. 2013.
U.S. Appl. No. 13/910,554, filed Dec. 2013.
Database WPI, Week 198731, Thomson Scientific, London, GA; AN 1987-218358 (XP002664153), & JP 62 145076 A (KOA Corp) Jun. 29, 1987.
International Search Report for PCT/EP2011/059848—Jun. 14, 2011, dated Jul. 25, 2011.

(Continued)

*Primary Examiner* — Andrew D Kosar
*Assistant Examiner* — John S Kenyon
(74) *Attorney, Agent, or Firm* — Drinker Biddle & Reath LLP

(57) ABSTRACT

A process for preparing a cyclic tertiary amine of the formula I

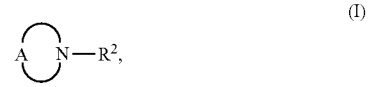

(I)

where
A is a $C_4$-alkylene group, a $C_5$-alkylene group or a $-(CH_2)_2-B-(CH_2)_2-$ group, where B is oxygen (O) or an $N-R^1$ radical and $R^1$ is $C_1$-$C_5$-alkyl, aryl or $C_5$-$C_7$-cycloalkyl, and the radical $R^2$ is a linear or branched $C_2$-$C_{16}$-alkyl, $C_5$-$C_7$-cycloalkyl or $C_7$-$C_{20}$-aralkyl, in which (i) an amino alcohol II from the group consisting of 1,4-aminobutanol, 1,5-aminopentanol, aminodiglycol (ADG) and aminoethylethanolamine of the formula IIa

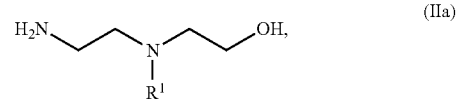

(IIa)

where $R^1$ is as defined above or hydrogen (H), in which case $R^1=R^2$ in the amine I, is reacted with a primary or secondary alcohol $R^2OH$ (III) at a temperature in the range from 150 to 270° C. in the liquid phase in the presence of a copper-comprising heterogeneous catalyst in a reactor.

25 Claims, No Drawings

(56) References Cited

U.S. PATENT DOCUMENTS

| | | | |
|---|---|---|---|
| 5,847,131 A | 12/1998 | Simon et al. | |
| 6,187,957 B1 | 2/2001 | Meyer et al. | |
| 6,448,457 B1 | 9/2002 | Hesse et al. | |
| 7,405,327 B2 * | 7/2008 | Haese et al. | 564/472 |
| 8,436,169 B2 | 5/2013 | Wigbers et al. | |
| 8,450,530 B2 | 5/2013 | Mueller et al. | |
| 2003/0089591 A1 | 5/2003 | Wolfert et al. | |
| 2005/0000791 A1 | 1/2005 | Wolfert et al. | |
| 2007/0232833 A1 | 10/2007 | Haese et al. | |
| 2008/0064882 A1 | 3/2008 | Huber-Dirr et al. | |
| 2008/0255351 A1 | 10/2008 | Hoffer et al. | |
| 2008/0299390 A1 | 12/2008 | Houssin et al. | |
| 2009/0286977 A1 | 11/2009 | Kubanek et al. | |
| 2010/0274010 A1 | 10/2010 | Kubanek et al. | |
| 2010/0274055 A1 | 10/2010 | Kubanek et al. | |
| 2011/0054167 A1 | 3/2011 | Kubanek et al. | |
| 2011/0137029 A1 | 6/2011 | Kubanek et al. | |
| 2011/0137030 A1 | 6/2011 | Kubanek et al. | |
| 2011/0172430 A1 * | 7/2011 | Ernst et al. | 546/184 |
| 2011/0218270 A1 | 9/2011 | Suter et al. | |
| 2011/0218323 A1 | 9/2011 | Dahmen et al. | |
| 2011/0288338 A1 | 11/2011 | Wigbers et al. | |
| 2012/0035049 A1 | 2/2012 | Kubanek et al. | |
| 2012/0035399 A1 | 2/2012 | Abillard et al. | |
| 2012/0157679 A1 * | 6/2012 | Wigbers et al. | 544/178 |

FOREIGN PATENT DOCUMENTS

| | | |
|---|---|---|
| CN | 1634896 A | 7/2005 |
| CN | 1962649 A | 5/2007 |
| CN | 102101847 A | 6/2011 |
| CN | 102304101 A | 1/2012 |
| DE | 917 784 C | 9/1954 |
| DE | 941 909 C | 4/1956 |
| DE | 1954546 A1 | 5/1971 |
| DE | 2125039 A1 | 12/1971 |
| DE | 1953263 A1 | 2/1972 |
| DE | 2445303 A1 | 4/1976 |
| DE | 26 28 087 A1 | 1/1977 |
| DE | 2706826 A1 | 9/1977 |
| DE | 3611230 A1 | 10/1987 |
| DE | 40 21 230 A1 | 1/1991 |
| DE | 4 028 295 A1 | 3/1992 |
| DE | 19809418 A1 | 9/1999 |
| DE | 19859776 A1 | 6/2000 |
| DE | 10218849 A1 | 11/2003 |
| EP | 70 512 A1 | 1/1983 |
| EP | 75940 A1 | 4/1983 |
| EP | 0137478 A2 | 4/1985 |
| EP | 0227904 A1 | 7/1987 |
| EP | 0235651 A1 | 9/1987 |
| EP | 0257443 A1 | 3/1988 |
| EP | 382049 A1 | 8/1990 |
| EP | 0434062 A1 | 6/1991 |
| EP | 440829 A1 | 8/1991 |
| EP | 446783 A2 | 9/1991 |
| EP | 514 692 A2 | 11/1992 |
| EP | 552 463 A1 | 7/1993 |
| EP | 599 180 A1 | 6/1994 |
| EP | 673 918 A1 | 9/1995 |
| EP | 696572 A1 | 2/1996 |
| EP | 0816350 A1 | 1/1998 |
| EP | 1312599 A1 | 5/2003 |
| EP | 1312600 A1 | 5/2003 |
| GB | 1512797 A | 6/1978 |
| JP | 62145076 A | 6/1987 |
| WO | WO-92/04119 A1 | 3/1992 |
| WO | WO-03/051508 A1 | 6/2003 |
| WO | WO-2004/085356 A1 | 10/2004 |
| WO | WO-2005/110969 A1 | 11/2005 |
| WO | WO-2006/005505 A1 | 1/2006 |
| WO | WO-2006/114417 A2 | 11/2006 |
| WO | WO-2007/036496 A1 | 4/2007 |
| WO | WO-2008/006750 A1 | 1/2008 |
| WO | WO-2008/006754 A1 | 1/2008 |
| WO | WO-2009/027249 A2 | 3/2009 |
| WO | WO-2009/080506 A1 | 7/2009 |
| WO | WO-2009/080507 A1 | 7/2009 |
| WO | WO-2009/080508 A1 | 7/2009 |
| WO | WO-2010/031719 A1 | 3/2010 |
| WO | WO-2010/052181 A2 | 5/2010 |
| WO | WO-2010/054988 A2 | 5/2010 |
| WO | WO-2010/069856 A1 | 6/2010 |
| WO | WO-2010/089265 A2 | 8/2010 |
| WO | WO-2010/089266 A2 | 8/2010 |
| WO | WO-2010/089346 A2 | 8/2010 |
| WO | WO-2010/103062 A1 | 9/2010 |
| WO | WO-2010/106133 A1 | 9/2010 |
| WO | WO-2010/115759 A2 | 10/2010 |
| WO | WO-2010/146009 A1 | 12/2010 |
| WO | WO-2011/067199 A1 | 6/2011 |
| WO | WO-2011/067200 A1 | 6/2011 |
| WO | WO-2011/082967 A1 | 7/2011 |
| WO | WO-2011/082994 A1 | 7/2011 |
| WO | WO-2011/107512 A1 | 9/2011 |
| WO | WO-2011/115759 A1 | 9/2011 |
| WO | WO-2011/157710 A1 | 12/2011 |
| WO | WO-2012/049101 A1 | 4/2012 |

OTHER PUBLICATIONS

International Search Report for PCT/EP2011/068700, mailed Feb. 17, 2012.
U.S. Appl. No. 13/158,667, filed Jun. 13, 2011, Wigbers et al.
U.S. Appl. No. 13/127,828, filed Aug. 5, 2011, Wigbers et al.
U.S. Appl. No. 13/080,080, filed Apr. 5, 2011.
U.S. Appl. No. 13/080,885, filed Apr. 6, 2011.
U.S. Appl. No. 13/112,161, filed Jun. 4, 2013.
U.S. Appl. No. 13/116,649, filed May 26, 2011.

* cited by examiner

PROCESS FOR PREPARING A CYCLIC TERTIARY AMINE

CROSS-REFERENCE TO RELATED APPLICATIONS

This application claims the benefit of U.S. Provisional Application 61/392,960, filed Oct. 14, 2010, which is incorporated by reference.

The present invention relates to a process for preparing a cyclic tertiary amine of the formula I

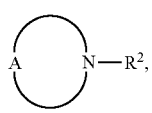

where

A is a $C_4$-alkylene group, a $C_5$-alkylene group or a $-(CH_2)_2-B-(CH_2)2-$ group, where B is oxygen (O) or an $N-R^1$ radical and $R^1$ is $C_1$-$C_5$-alkyl, aryl or $C_5$-$C_7$-cycloalkyl, and the radical $R^2$ is a linear or branched $C_2$-$C_{16}$-alkyl, $C_5$-$C_7$-cycloalkyl or $C_7$-$C_{20}$-aralkyl.

BACKGROUND OF THE INVENTION

Tertiary amines have great importance in the chemical industry for the production of process chemicals, catalsyts and intermediates for higher value-added products.

EP 257 443 A1 (BASF AG) discloses the preparation of trialkylamines (e.g. dimethylethylamine) by reacting ammonia or primary amines with primary monohydric aliphatic alcohols having from 2 to 24 carbon atoms, preferably in the presence of hydrogen and in the presence of a hydrogenation/dehydrogenation catalyst. The reaction is carried out continuously in the liquid phase at a total pressure of from 50 to 300 bar and a molar excess of from 1 to 15 mol of the alcohol over the ammonia or the primary amine. In addition, the alkylation is carried out in the presence of alkali metal and/or alkaline earth metal oxides and/or hydroxides. The hydrogenation/dehydrogenation catalyst comprises essentially copper.

In examples 1 and 3, ammonia is reacted with ethanol or n-butanol in the presence of sodium hydroxide to form tri-ethylamine or tri-n-butylamine. The reaction is carried out at from 230 to 250° C., total pressures of 200 bar and hydrogen partial pressures of >150 bar or 120 bar. Apart from the tertiary amines as target products, only small amounts of secondary amines are formed.

In example 2, the primary amine n-pentylamine is used instead of ammonia and is reacted continuously with n-pentanol in the presence of sodium hydroxide to form tri-n-pentylamine. The molar ratio of n-pentylamine to n-pentanol is 1:4. The reaction temperature is 230-235° C., the total pressure is 60 bar, of which about 10 bar is due to the hydrogen partial pressure. The molar ratio of tri-n-pentylamine to di-n-pentylamine in the reaction product mixture was 1:0.1. Excess n-pentanol was not recirculated to the synthesis stage.

According to claim 4, $C_1$-$C_{24}$-alcohols are used in pure form or in the form of their mixtures.

In a similar way, dimethylamine is reacted with ethanol or n-butanol in the liquid phase to form dimethylethylamine or dimethyl-n-butylamine in EP 227 904 A1 (BASF AG). The reaction is carried out in the presence of alkali metal hydroxide and a catalyst which comprises essentially only copper as active metal or is a pure copper catalyst. It is possible to use monohydric aliphatic alcohols having from 2 to 4 carbon atoms.

A disadvantage of working according to EP 257 443 A1 and EP 227 904 A1 is that the alkali metal and/or alkaline earth metal oxides and/or alkali metal or alkaline earth metal hydroxides added to the reaction mixture have to be separated off from the reaction product mixture again after the alkylation reaction.

U.S. Pat. No. 4,910,304 A (BASF AG) discloses the preparation of N-methylpiperidine and N-methyl-morpholine by reaction of pentanediol or diethylene glycol (DEG) with methylamine and 45% strength aqueous KOH solution over an all-active Cu/Al catalyst at 245° C. and 250 bar.

EP 137 478 A (BASF AG) relates to processes for preparing N-methylpiperidine or N-methyl-morpholine by catalytic amination of pentanediol by means of methylamine in the gas phase at from 5 to 25 bar over a copper-comprising catalyst which has been produced by heat treatment of a basic carbonate comprising copper and aluminum.

EP 235 651 A1 (BASF AG) teaches a process for preparing N-methylpiperazine from diethanolamine and methylamine over metal-comprising catalysts. The reaction is carried out in the liquid phase (downflow mode) (page 3, last paragraph). According to an example, a $Cu/Al_2O_3$ catalyst is used.

EP 816 350 A1 (BASF AG) describes processes for preparing N-methylpiperidine and N-methylmorpholine by reacting a primary amine with a diol over a copper catalyst which has been obtained by impregnating $SiO_2$ spheres with a basic copper carbonate, in the liquid or gas phase.

U.S. Pat. No. 4,739,051 A (BASF AG) teaches the preparation of morpholine and piperidine by reaction of DEG or pentanediol with ammonia under hydrogenation conditions in the gas phase at atmospheric pressure and 200° C. over an all-active Cu/Ni/Al catalyst.

EP 514 692 A2 (BASF AG) discloses processes for preparing amines from alcohols in the presence of catalysts comprising copper and nickel and zirconium oxide and/or aluminum oxide.

EP 440 829 A1 (U.S. Pat. No. 4,910,304) (BASF AG) describes the amination of diols over copper catalysts. The reaction is carried out in the liquid phase (downflow mode) (page 3, last pararaph). Suitable catalysts are the catalysts which are disclosed in DE 24 45 303 A (BASF AG) and can be obtained by heat treatment of a basic carbonate comprising copper and aluminum of the general composition $Cu_mAl_6(CO_3)_{0.5m}O_3(OH)_{m+12}$, where m is any, even not integral, number in the range from 2 to 6, for example the copper-comprising precipitated catalyst which is disclosed in loc. cit., example 1, and is produced by treating a solution of copper nitrate and aluminum nitrate with sodium bicarbonate and subsequently washing, drying and heat-treating the precipitate.

WO 07/036496 A1 (BASF AG) describes the reaction of diethylene glycol with ammonia in the presence of Cu—Ni—Co catalysts.

WO 05/110969 A1 (BASF AG) describes a process for the continuous preparation of an amine by reaction of a primary or secondary alcohol, aldehyde and/or ketone with hydrogen and a nitrogen compound selected from the group consisting of ammonia, primary and secondary amines at a temperature in the range from 60 to 300° C. in the presence of a copper-comprising catalyst, where the catalytically active composition of the catalyst before reduction with hydrogen comprises from 20 to 85% by weight of aluminum oxide ($Al_2O_3$), zirconium dioxide ($ZrO_2$), titanium dioxide ($TiO_2$) and/or silicon dioxide ($SiO_2$) and the reaction is carried out isothermally in the gas phase in a tube reactor.

WO 2010/031719 A1 (BASF SE) relates to a process for the continuous preparation of an amine by reaction of a primary or secondary alcohol, aldehyde and/or ketone with hydrogen and a nitrogen compound selected from the group consisting of ammonia, primary and secondary amines at a temperature in the range from 60 to 300° C. in the presence of a catalyst comprising copper and aluminum oxide, where the reaction is carried out in the gas phase and the catalytically active composition of the catalyst before reduction with hydrogen comprises aluminum oxide and oxygen-comprising compounds of copper and the shaped catalyst body is specified.

The earlier EP application number 10166017.3 of Jun. 15, 2010 (BASF SE) relates to a process for preparing a cyclic tertiary methylamine of the formula

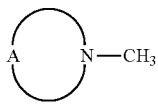

where A is a $C_4$-alkylene group, a $C_5$-alkylene group or a —$(CH_2)_2$—B—$(CH_2)_2$ group, where B is oxygen (O) or an N—$R^1$ radical and $R^1$ is $C_1$-$C_5$-alkyl, aryl or $C_5$-$C_7$-cycloalkyl.

DETAILED DESCRIPTION OF THE INVENTION

It is an object of the present invention to remedy the disadvantages of the prior art and to discover an improved economical process for preparing a cyclic tertiary amine. In particular, the process should make better yields, space-time yields (STY) and selectivities possible, especially without the addition of hydrogen.

[Space-time yields are reported in 'amount of product/(catalyst volume·time)' (kg/($l_{cat}$·h)) and/or 'amount of product/(reactor volume·time)' (kg/($l_{reactor}$·h))].

We have accordingly found a process for preparing a cyclic tertiary amine of the formula I

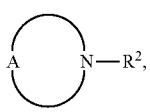

(I)

where

A is a $C_4$-alkylene group, a $C_5$-alkylene group or a —$(CH_2)_2$—B—$(CH_2)_2$—group, where B is oxygen (O) or an N—$R^1$ radical and $R^1$ is $C_1$-$C_5$-alkyl, aryl or $C_5$-$C_7$-cycloalkyl, and the radical $R^2$ is a linear or branched $C_2$-$C_{16}$-alkyl, $C_5$-$C_7$-cycloalkyl or $C_7$-$C_{20}$-aralkyl, wherein (i) an amino alcohol II from the group consisting of 1,4-aminobutanol, 1,5-aminopentanol, aminodiglycol (ADG) and aminoethylethanolamine of the formula IIa

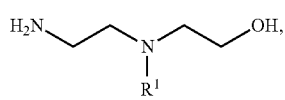

(IIa)

where $R^1$ is as defined above or hydrogen (H), in which case $R^1=R^2$ in the amine I, is reacted with a primary or secondary alcohol $R^2OH$ (III) at a temperature in the range from 150 to 270° C. in the liquid phase in the presence of a copper-comprising heterogeneous catalyst in a reactor.

Preference is given to unreacted alcohol III or a homoazeotrope or heteroazeotrope of unreacted alcohol (III) and water being separated off from the output from the reaction (reaction step (i)) by distillation in a first distillation unit in a subsequent step (ii) and the alcohol III, in the case of a homoazeotrope being present, being recirculated, after separation of the azeotrope, to reaction step (i).

If the alcohol $R^2OH$ distills off, for example, at the top, the alcohol can be recirculated to reaction step (i). If, for example in the case of n-butanol, a heteroazeotrope of n-butanol and water goes over at the top, the two liquid phases are separated after condensation of the reaction mixture: n-butanol is recirculated to the cyclizing alkylation, water is discharged. If, for example in the case of ethanol, a homoazeotrope of ethanol and water goes over at the top, this azeotrope subsequently has to be separated by known methods. The alcohol is subsequently recirculated to the cyclizing alkylation.

Further preference is given to water of reaction being removed from the bottom product from the first distillation unit by extraction with aqueous alkali metal or alkaline earth metal hydroxide solution or by azeotropic distillation with a hydrocarbon in a second distillation unit in a subsequent step (iii), and (iv) the resulting output being fractionally distilled to give tertiary amine I.

The process of the invention makes it possible to carry out the substeps of cyclic alkylation, namely cyclization and alkylation, in one reaction step. Here, the amino alcohols II, IIa are converted with high conversions and in high yields into the cyclic tertiary amine I. Recirculation of incompletely alkylated or cyclized intermediates is therefore generally not necessary. However, it is possible.

The reaction temperature in the preparation of the tertiary amine I is from 150 to 270° C., preferably from 170 to 250° C., particularly preferably from 180 to 230° C.

According to the stoichiometry of the alkylation by means of the alcohol III, no hydrogen has to be introduced. Accordingly, no hydrogen ($H_2$) is fed into the reactor in reaction step (i) in one embodiment of the process.

However, it can be advantageous to introduce hydrogen into the reaction mixture either continuously or from time to time in order to keep the activity of the hydrogenation catalyst constant over very long periods of time.

The reaction pressure in the reactor is made up, at the respective reaction temperature, of the partial pressures of the starting materials and the reaction products, and optionally solvents and added hydrogen. The pressure is increased to the desired reaction pressure by injection of hydrogen.

The total pressure (absolute) is preferably from 50 to 150 bar, preferably from 60 to 130 bar, particularly preferably from 70 to 120 bar.

If hydrogen is used, the hydrogen partial pressure is in particular from 0.01 to 130 bar, preferably from 0.1 to 100 bar, particularly preferably from 1 to 80 bar.

If the alkylation is carried out continuously, the space-time yield is in particular from 0.01 to 5 kg/($l_{cat}$·h), preferably from 0.05 to 3 kg/($l_{cat}$·h), particularly preferably from 0.1 to 1.0 kg/($l_{cat}$·h). ($l_{cat.}$=bed volume of catalyst)

The primary or secondary alcohol III is preferably used in a distinct excess over the amino alcohol (II, IIa) and can serve as reactant and at the same time as solvent. The molar ratio of amino alcohol to alcohol III is in particular 1:25, preferably 2:20, particularly preferably 3:15. A high molar ratio can have a positive effect on the selectivity of the tertiary amines I, as long as the excess of alcohol III does not adversely affect the intramolecular cyclization.

The radical $R^2$ is linear or branched $C_2$-$C_{16}$-alkyl, preferably linear or branched $C_2$-$C_8$-alkyl, $C_5$-$C_7$-cycloalkyl or $C_7$-$C_{20}$-aralkyl, preferably $C_7$-$C_{12}$-phenylalkyl.

Preferred primary and secondary alcohols $R^2OH$ of the formula III are selected from the group consisting of ethanol, n-propanol, i-propanol, i-butanol, sec-butanol, n-butanol, 2-methyl-1-propanol, pivalyl alcohol, n-pentanol, n-hexanol, 2-ethylhexanol, 2-methyl-1-pentanol, 3-methyl-1-pentanol, 4-methyl-1-pentanol, n-octanol, n-decanol, n-undecanol, n-dodecanol, 2-phenyl-ethanol, 2-cyclopentylethanol, 2-cyclohexylethanol, 2-cycloheptylethanol, methylphenylethanol, benzyl alcohol, methylbenzyl alcohol and mixtures of these alcohols.

The aralkyl or phenylalkyl radicals can be substituted in the o, m and/or p position by aliphatic radicals having from 1 to 4 carbon atoms and/or methoxy groups. The aralkyl or phenylalkyl radicals preferably bear substituents selected from the group consisting of methoxy, methyl, ethyl, n-propyl, i-propyl, n-butyl, i-butyl, sec-butyl and tert-butyl groups. Examples are benzyl, p-methoxybenzyl, 3,4-dimethoxybenzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl.

Particularly preferred primary and secondary alcohols of the formula III are selected from the group consisting of ethanol, n-propanol, i-propanol, n-butanol, 2-methyl-1-propanol, n-pentanol and mixtures of these alcohols.

Very particular preference is given to primary alcohols of the formula III selected from the group consisting of ethanol, n-propanol, n-butanol, 2-methyl-1-propanol and mixtures of these alcohols. Especial preference is given to the primary alcohol being ethanol ($R^2$=ethyl).

However, it can also be advantageous for a solvent which is inert under the reaction conditions to be additionally used. Possibilities here are aliphatic, cycloaliphatic or aromatic solvents. Examples are n-hexane, n-octane, cyclohexane, methylcyclohexane, toluene, o-, m- or p-xylene or mixtures of these compounds.

The mixture of amino alcohol, alcohol III and inert solvent can comprise from 20 to 70% by weight, preferably from 30 to 60% by weight, of inert solvent.

In a specific embodiment, the reaction is carried out in a plurality of reactors (e.g. 2, 3, 4, 5, etc.) reactors. Preference is given to a combination of two reactors. Here, it is possible to use identical or different reactors. The reactors can be connected to one another in any way, e.g. in parallel or in series. In a preferred embodiment, two reactors connected in series are used. If a plurality of reactors is used, these can have identical or different temperatures. The temperature in the n-th reactor is preferably at least 10° C. higher, particularly preferably at least 20° C. higher, in particular at least 30° C. higher, than the temperature in the (n-1)-th reactor. When using a plurality of reactors, the reaction pressure can be identical or different in the individual reactors. In a specific embodiment, only part of the reactors comprises catalyst. Thus, for example, it is possible to use a combination of two reactors of which only one comprises catalyst. In this variant, the reaction mixture can firstly be preheated in a reactor without catalyst and subsequently be transferred to a reactor comprising catalyst for the reaction. To transfer the reaction mixture, it is possible to use, for example, an inert gas such as nitrogen and noble gases or hydrogen by means of which the mixture is pushed from one reactor into another reactor. In addition, the gas can also serve to set the desired reaction pressure.

Suitable catalysts are in principle hydrogenation catalysts, preferably copper-comprising, heterogeneous catalysts.

Many copper-comprising catalysts which can additionally comprise at least one further element of main group I, II, III, IV or V, of transition group I, II, IV, V, VII or VIII and of the lanthanides (IUPAC: groups 1 to 15 and the lanthanides), in particular Ca, Mg, Al, La, Ti, Zr, Cr, Mo, W, Mn, Ni, Co, Zn and combinations thereof are suitable in principle. A specific embodiment of advantageous catalysts is represented by Raney catalysts, especially Raney copper and copper-comprising metal alloys in the form of a Raney catalyst. Preference is given to Raney catalysts whose metal component comprises at least 95% by weight, in particular at least 99% by weight, of copper. Raney copper can be produced in a manner known per se by treating copper-aluminum alloys with alkali metal hydroxides.

A further specific embodiment of catalysts which are particularly advantageously used comprises catalysts which comprise copper in oxidic form and also optionally in elemental form.

Suitable catalysts are, for example, catalysts which comprise nickel and copper and also other metals as active constituents on a silica support. Such catalysts are described, for example, in DE 26 28 087 A. The active composition of these catalysts comprises, in particular, from 40 to 80% by weight of nickel, from 10 to 50% by weight of copper and from 2 to 10% by weight of manganese. EP 434 062 A describes hydrogenation catalysts which can be obtained by reduction of a precursor composed of oxides of copper, aluminum and at least one further metal selected from among magnesium, zinc, titanium, zirconium, tin, nickel and cobalt. The hydrogenation catalysts described in DE 102 18 849 A, which comprise from 0.1 to 10% by weight of chromium, calculated as $Cr_2O_3$, from 0.1 to 10% by weight of calcium, calculated as CaOx, and from 5 to 20% by weight of copper, calculated as CuO, deposited on a silicon dioxide support material, in each case based on the total weight of the calcined catalyst, are also suitable. DE 40 21 230 A discloses copper-zirconium oxide catalysts in which the ratio of copper atoms to zirconium atoms, expressed as a weight ratio, is from 1:9 to 9:1. DE 4 028 295 A describes a suitable copper-manganese hydrogenation catalyst system. EP 552 463 A describes catalysts where the oxidic form corresponds essentially to the composition $Cu_aAl_bZr_cMn_dO_x$, where the following relationships apply: a>0; b>0; c≥0; d>0; a>b/2; b>a/4; a>c; a>d; and x denotes the number of oxygen ions required to achieve electric neutrality per formula unit. EP 552 463 A also describes catalysts having a relatively small proportion of aluminum oxide. The catalyst according to this embodiment corresponds essentially to the composition $Cu_aAl_bZr_cMn_dO_x$, where the following relationships apply: a>0; a/40≤b≤a/4; c≥0; d>0; a>c; 0.5d≤a≤0.95d and x denotes the number of oxygen ions required to achieve electric neutrality per formula unit. WO 2006/005505 A describes shaped catalyst bodies which are particularly suitable for use in the process of the invention. In a preferred embodiment, the oxidic catalyst material comprises (a) copper oxide in a proportion in the range 50≤x≤80% by weight, preferably 55≤x≤75% by weight, (b) aluminum oxide in a proportion in the range 15≤y≤35% by weight, preferably 20≤y≤30% by weight, and (c) at least one of the oxides of lanthanum, tungsten, molybdenum, titanium or zirconium, preferably of lanthanum and/or tungsten, in a proportion in the range 2≤z≤20% by weight, preferably 3≤z≤15% by weight, in each case based on the total weight of the oxidic material after calcination, where: 80≤x+y+z≤100, in particular 95≤x+y+z≤100.

Preferred catalysts comprise the following metals in oxidic form, reduced form (elemental form) or a combination thereof. Metals which are stable in more than one oxidation state can be used entirely in one of the oxidation states or in different oxidation states:

Cu
Cu, Ti
Cu, Zr
Cu, Mn
Cu, Al
Cu, Ni, Mn
Cu, Al, at least one further metal selected from among La, W, Mo, Mn, Zn, Ti, Zr, Sn, Ni, Co
Cu, Zn, Zr
Cu, Cr, Ca
Cu, Cr, C
Cu, Al, Mn, optionally Zr.

As inert support material for the catalysts used according to the invention, it is possible to use virtually all support materials of the prior art as are advantageously used in the production of supported catalysts, for example $SiO_2$ (quartz), porcelain, magnesium oxide, tin dioxide, silicon carbide, $TiO_2$ (rutile, anatase), $Al_2O_3$ (alumina), aluminum silicate, steatite (magnesium silicate), zirconium silicate, cerium silicate or mixtures of these support materials. Preferred support materials are aluminum oxide and silicon dioxide.

In the preferred embodiment of the process of the invention, copper catalysts as described in DE 2 445 303 A1 (BASF AG) are used. They can be regarded as amorphous products of thermal decomposition and reduction of basic copper aluminum carbonates and be obtained by precipitating dilute or moderately concentrated, advantageously less than 3-molar, solutions of copper salts and aluminum salts by means of alkali metal carbonate at pH 8-10 and decomposing the resulting precipitants, before or after appropriate shaping, at a temperature of 350-600° C. Customary reduction, preferably in the presence of the alcohol used in the later reaction, gives highly active catalysts which are best suited for the present process.

In the suspension mode which is likewise possible in the process of the invention, the reduced copper catalyst is suspended in the reaction components alcohol and amines. Suitable catalysts are, for example, Raney copper or the above-described copper catalysts in powdered form. However, preference is given to a copper material which is obtained by heating copper formate to 200-250° C. in the presence of an alcohol and dialkylamine. The way in which such a catalyst is formed is described, for example, in EP 70 512 A.

The catalysts can be used as shaped bodies, e.g. in the form of spheres, rings, cylinders, cubes, cuboids or other geometric bodies. Unsupported catalysts can be shaped by conventional methods, e.g. by extrusion, tableting, etc. The shape of supported catalysts is determined by the shape of the support. As an alternative, the support can be subjected to a shaping process before or after application of the catalytically active component(s). The catalysts can be used, for example, in the form of pressed cylinders, pellets, pastilles, wagon wheels, rings, stars or extrudates such as solid extrudates, polylobal extrudates, hollow extrudates and honeycomb bodies or other geometric bodies.

In the process of the invention, the catalysts are particularly preferably used in the form of catalysts which comprise only catalytically active composition and optionally a shaping aid (e.g. graphite or stearic acid) if the catalyst is used as shaped bodies, i.e. do not comprise any further catalytically active accompanying materials.

In this context, oxidic support material, particularly preferably aluminum oxide ($Al_2O_3$), is considered to belong to the catalytically active composition.

The catalysts are preferably used by arranging the catalytically active composition as shaped catalyst bodies, e.g. as pellets, spheres, rings, extrudates, in the reactor after milling, mixing with shaping aids, shaping and heat treatment.

The reported concentrations (in % by weight) of the components of the catalyst are in each case based, unless indicated otherwise, on the catalytically active composition of the finished catalyst after its last heat treatment and before reduction with hydrogen.

The catalytically active composition of the catalyst after its last heat treatment and before reduction with hydrogen is defined as the sum of the masses of the catalytically active constituents and the abovementioned catalyst support material and preferably comprises essentially the following constituents:

aluminum oxide ($Al_2O_3$) and oxygen-comprising compounds of copper and preferably oxygen-comprising compounds of sodium.

The sum of the abovementioned constituents of the catalytically active composition, calculated as $Al_2O_3$, CuO and $Na_2O$, is usually from 70 to 100% by weight, preferably from 80 to 100% by weight, particularly preferably from 90 to 100% by weight, more preferably from 98 to 100% by weight, more preferably ≥99% by weight, very particularly preferably 100% by weight.

The catalytically active composition of the catalysts used in the process of the invention can further comprise one or more elements (oxidation state 0) or inorganic or organic compounds thereof selected from groups IA to VIA and IB to VIIB and VIII of the Periodic Table.

Examples of such elements and compounds thereof are:
transition metals such as Ni and NiO, Co and CoO, Re and rhenium oxides, Mn and $MnO_2$, Mo and molybdenum oxides, W and tungsten oxides, Ta and tantalum oxides, Nb and niobium oxides or niobium oxalate, V and vanadium oxides or vanadyl pyrophosphate; lanthanides such as Ce and $CeO_2$ or Pr and $Pr_2O_3$; alkali metal oxides such as $K_2O$; alkali metal carbonates such as $Na_2CO_3$; alkaline earth metal oxides such as CaO, SrO; alkaline earth metal carbonates such as $MgCO_3$, $CaCO_3$ and $BaCO_3$; boron oxide ($B_2O_3$).

The catalytically active composition of the catalysts used in the process of the invention after its last heat treatment and before reduction with hydrogen comprises, in particular, from 25 to 80% by weight, preferably from 30 to 70% by weight, particularly preferably from 35 to 60% by weight, of aluminum oxide ($Al2O_3$) and from 20 to 75% by weight, preferably from 30 to 70% by weight, particularly preferably from 40 to 65% by weight, very particularly preferably from 45 to 60% by weight, of oxygen-comprising compounds of copper, calculated as CuO, from 0 to 2% by weight, preferably from 0.05 to 1% by weight, particularly preferably from 0.1 to 0.5% by weight, of oxygen-comprising compounds of sodium, calculated as $Na_2O$, less than 5% by weight, e.g. from 0.1 to 4% by weight, preferably less than 1% by weight, e.g. from 0 to 0.8% by weight, of oxygen-comprising compounds of nickel, calculated as NiO.

The catalytically active composition of the catalyst before reduction with hydrogen particularly preferably comprises less than 1% by weight, e.g. from 0 to 0.5% by weight, of oxygen-comprising compounds of cobalt, calculated as CoO.

The catalytically active composition of the catalyst used in the process of the invention very particularly preferably comprises no nickel, no cobalt and/or no ruthenium, in each case neither in the metallic (oxidation state 0) nor an ionic, in particular oxidized, form.

The oxygen-comprising compounds of copper are, in particular, copper(I) oxide and copper(II) oxide, preferably copper(II) oxide.

The catalytically active composition of the catalyst used in the process of the invention very particularly preferably does not contain any zirconium dioxide ($ZrO_2$), titanium dioxide ($TiO_2$) and/or silicon dioxide ($SiO_2$).

In a particularly preferred embodiment, the catalytically active composition of the catalysts used in the process of the invention does not contain any further catalytically active component, neither in elemental form nor in ionic form.

In the particularly preferred embodiment, the catalytically active composition is not doped with further metals or metal compounds.

However, usual accompanying trace elements originating from the isolation of Cu, optionally Ni, metal are preferably excluded from this.

Various processes are possible for producing the catalysts used in the process of the invention. They can be obtained, for example, by peptizing pulverulent mixtures of the hydroxides, carbonates, oxides and/or other salts of the components aluminum, copper, optionally sodium by means of water and subsequently extruding and heat treating the composition obtained in this way.

The catalysts which are preferably used in the process of the invention can also be produced by impregnation of aluminum oxide ($Al_2O_3$), which is present, for example, in the form of powder or shaped pellets.

Here, aluminum oxide can be used in various modifications, with preference being given to α- (alpha), α- (gamma) or θ-$Al_2O_3$ (theta-$Al_2O_3$). Particular preference is given to using γ-$Al_2O_3$.

The production of shaped bodies of aluminum oxide can be carried out by the usual processes.

The impregnation of the aluminum oxide is likewise carried out by the usual processes, as described, for example, in EP 599 180 A, EP 673 918 A or A. B. Stiles, Catalyst Manufacture—Laboratory and Commercial Preparations, Marcel Dekker, New York (1983), by applying an appropriate metal salt solution in one or more impregnation steps, using, for example, appropriate nitrates, acetates or chlorides as metal salts. The composition is dried and optionally calcined after the impregnation.

The impregnation can be carried out by the "incipient wetness" method in which the inorganic oxide (i.e. aluminum oxide) is moistened with the impregnation solution according to its water absorption capacity up to but not above saturation. However, the impregnation can also be carried out in supernatant solution.

In the case of multistage impregnation processes, it is advantageous to dry and optionally calcine the impregnated material between individual impregnation steps. Multistage impregnation is particularly advantageous when a relatively large amount of metal is to be deposited on the inorganic oxide.

To apply a plurality of metal components to the inorganic oxide, the impregnation can be carried out simultaneously with optionally all metal salts or in any order of the optionally individual metal salts in succession.

Preference is given to using precipitation methods for producing the catalysts which are preferably used in the process of the invention. Thus, they can be obtained, for example, by coprecipitation of the components from an aqueous salt solution by means of mineral bases in the presence of a slurry of a sparingly soluble, oxygen-comprising aluminum compound and subsequent washing, drying and calcination of the precipitate obtained. As sparingly soluble, oxygen-comprising aluminum compound, it is possible to use, for example, aluminum oxide. The slurries of the sparingly soluble aluminum compound can be produced by suspending finely particulate powder of this compound in water with vigorous stirring. These slurries are advantageously obtained by precipitating the sparingly soluble aluminum compound from aqueous aluminum salt solutions by means of mineral bases.

The catalysts which are preferably used in the process of the invention are preferably produced by coprecipitation (mixed precipitation) of all their components. For this purpose, an aqueous salt solution comprising the catalyst components is advantageously admixed, hot and while stirring, with an aqueous mineral base, in particular an alkali metal base, for example sodium carbonate, sodium hydroxide, potassium carbonate or potassium hydroxide, until precipitation is complete. The type of salts used is generally not critical: since the water-solubility of the salts is the most important thing in this procedure, a criterion is good water-solubility of the salts so that these relatively highly concentrated salt solutions can be produced. It is considered to be self evident that naturally only salts having anions which do not lead to interference, whether by causing undesirable precipitations or by making the precipitation difficult or preventing it entirely by formation of complexes, are chosen when selecting the salts of the individual components.

The precipitates obtained in these precipitation reactions are generally chemically nonuniform and comprise, inter alia, mixtures of the oxides, hydrated oxides, hydroxides, carbonates and insoluble and basic salts of the metal or metals used. It can be advantageous in terms of the filterability of the precipitates for them to be aged, i.e. for them to be left to stand for some time after the precipitation, optionally hot or with air being passed through.

The precipitates obtained by these precipitation processes are processed further in a conventional manner to give the catalysts used according to the invention. After washing, they are preferably dried at from 80 to 200° C., preferably from 100 to 150° C., and then calcined. Calcination is preferably carried out at temperatures in the range from 300 to 800° C., more preferably from 400 to 600° C., in particular from 450 to 550° C.

After calcination, the catalyst is advantageously conditioned, either by bringing it to a particular particle size by milling and/or by mixing it after milling with shaping aids such as graphite or stearic acid, pressing it by means of a press to give compacts, viz. pellets, and heat treating it. The heat treatment temperatures preferably correspond to the temperatures in the calcination.

The catalysts produced in this way comprise the catalytically active metals in the form of a mixture of their oxygen-comprising compounds, i.e. in particular as oxides and mixed oxides.

The catalysts produced in this way can be stored as such. Before use as catalysts, they are usually prereduced. However, they can also be used without prereduction, in which case they are then reduced under the conditions of the hydrogenative amination by the hydrogen present in the reactor.

To carry out the prereduction, the catalysts are firstly exposed to a nitrogen/hydrogen atmosphere at preferably from 150 to 200° C. over a period of, for example, from 12 to 20 hours and subsequently treated in a hydrogen atmosphere at preferably from 200 to 400° C. for up to about 24 hours. In this prereduction, part of the oxygen-comprising metal compound(s) present in the catalysts is/are reduced to the corresponding metal(s), so that these are present together with the various oxygen compounds in the active form of the catalyst.

The reaction as per the process of the invention is preferably carried out in a tube reactor.

In a monostream plant, the tube reactor in which the preferably isothermal reaction is carried out comprises a plurality of (e.g. two or three) individual tube reactors connected in series.

The preferably isothermal reaction as per the process of the invention is preferably carried out with a temperature deviation of not more than +/−8° C., particularly preferably not more than +/−5° C., in particular not more than +/−4° C., very particularly preferably not more than +/−3° C., e.g. not more than from +/−0 to +/−2° C. or not more than +/−0 to +/−1° C.

These temperature deviations relate to the respective temperatures in the respective catalyst bed, at the point of entry of the starting materials into the catalyst bed and at the point of exit of the reaction mixture from the catalyst bed.

It is possible to arrange a plurality of catalyst beds in parallel or in series.

If a plurality of catalyst beds are connected in series, the abovementioned temperature deviations relate, in the case of the isothermal mode of operation which is preferred according to the invention, to the respective temperature in the catalyst bed, at the point of entry of the starting materials into the first catalyst bed and at the point of exit of the reaction mixture from the last catalyst bed.

In a preferred embodiment, the temperature of the reactor tube is regulated from the outside by means of a stream of heat transfer medium, which can be, for example, an oil, a salt melt or another heat-transferring liquid.

The process of the invention is preferably carried out continuously, with the catalyst preferably being arranged as a fixed bed in the reactor. Here, the flow into the catalyst bed can be either from the top or from the bottom.

The water of reaction formed during the course of the reaction generally has no adverse effect on the conversion, the reaction rate, the selectivity and the operating life of the catalyst and is therefore advantageously removed from the reaction product, e.g. by distillation, only during work-up of the reaction product.

The liquid reaction output obtained after cooling and depressurization is optionally separated off from suspended catalysts. The catalyst-free reaction output comprises not only the target product, viz. the tertiary amine I, but also excess alcohol III and water formed. Depending on the number of alkylation steps, two or three mole of water are formed, depending on and based on the amino alcohol (II, IIa) used. In addition, any unreacted amino alcohol, intermediates which have not been fully alkylated and possibly small amounts of amino alcohol by-products may be present.

The work-up is carried out, in particular, by distillation.

In a continuous mode of operation, preference is given to amino alcohol (II, IIa) and recycle alcohol from step (ii) being introduced in two separate streams rather than a combined stream into the reactor of reaction step (i).

In particular, the recycle alcohol from step (ii) and the amino alcohol are each or as a mixture preheated to a temperature in the range from 20 to 240° C., in particular from 40 to 150° C., more particularly from 50 to 100° C., before introduction into the reactor of reaction step (i).

The bottom product from the removal of unreacted alcohol III by distillation can be extracted with from 20 to 50% strength by weight aqueous alkali metal hydroxide or alkaline earth metal hydroxide solution (e.g. sodium hydroxide solution) to separate off the water of reaction. The aqueous hydroxide solution is separated off by phase separation and discharged, and the organic phase is preferably distilled in a further distillation unit in such a way that the tertiary amine I is obtained as overhead product and high boilers (HB) are obtained as bottom product.

In a further preferred embodiment of the alkylation, the distillation bottoms after alcohol removal, which may already contain a hydrocarbon (in particular a $C_4$-$C_{10}$-hydrocarbon such as heptanes, octanes, cyclohexanes, cycloheptanes) as solvent, is fed to a further distillation unit. If necessary, a further amount of the hydrocarbon is fed into the further distillation unit. A two-phase hydrocarbon/water azeotrope is distilled off at the top by azeotropic distillation. In the phase separator P, the water phase is discharged and the hydrocarbon phase is returned to the top of the column. The stream from the bottom of the column is fed to a further distillation unit to isolate pure tertiary amine I.

The process of the invention makes it possible to prepare tertiary amines of the formula I

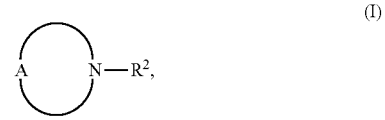

where

A is a $C_4$-alkylene group, a $C_5$-alkylene group or a —$(CH_2)_2$—B—$(CH_2)_2$— group, where B is oxygen (O) or an N—$R^1$ radical and $R^1$ is $C_1$-$C_5$-alkyl, aryl or $C_5$-$C_7$-cycloalkyl, and the radical $R^2$ is a linear or branched $C_2$-$C_{16}$-alkyl, $C_5$-$C_7$-cycloalkyl or $C_7$-$C_{20}$-aralkyl, by reacting an amino alcohol II from the group consisting of 1,4-aminobutanol, 1,5-aminopentanol, aminodiglycol (ADG) and aminoethylethanolamine of the formula IIa

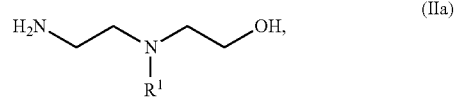

where $R^1$ is as defined above or hydrogen (H), in which case $R^1$=$R^2$ in the amine I, with a primary or secondary alcohol $R^2$OH (III).

Preference is given to preparing N-alkylpyrrolidine (alkyl=$R^2$) by reacting 1,4-aminobutanol with an alcohol $R^2$OH. In particular, $R^2$=ethyl.

Preference is also given to preparing N-alkylpiperidine (alkyl=$R^2$) by reacting 1,5-amino-pentanol with an alcohol $R^2$OH. In particular, $R^2$=ethyl.

Preference is also given to preparing N-alkylmorpholine (alkyl=$R^2$) by reacting aminodiglycol (ADG) with an alcohol $R^2$OH. In particular, $R^2$=ethyl.

Preference is additionally given to preparing N,N'-dialkylpiperazine of the formula V

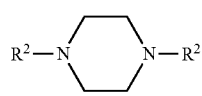
(V)

by reacting aminoethylethanolamine of the formula IIa

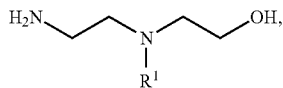
(IIa)

where $R^1$ is hydrogen (H), with an alcohol $R^2OH$. In particular, $R^2$=ethyl.

Preference is additionally given to preparing N,N'-dialkylpiperazine of the formula VI

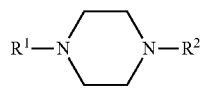
(VI)

by reacting aminoethylethanolamine of the formula IIa

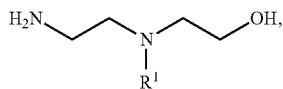
(IIa)

where $R^1$ is not hydrogen (H), with an alcohol $R^2OH$. In particular, $R^2$=ethyl. Preference is also given to $R^1$=methyl or ethyl.

The substituent $R^1$ in the compounds I and IIa has the following meanings:

$R^1$:
- $C_{1-5}$-alkyl, preferably $C_{1-3}$-alkyl, e.g. methyl, ethyl, n-propyl, isopropyl, n-butyl, isobutyl, sec-butyl, tert-butyl, n-pentyl, isopentyl, sec-pentyl, neopentyl, 1,2-dimethylpropyl, particularly preferably methyl, ethyl,
- $C_{5-7}$-cycloalkyl, preferably $C_{5-6}$-cycloalkyl, e.g. cyclopentyl, cyclohexyl, cycloheptyl,
- aryl such as phenyl, 1-naphthyl, 2-naphthyl, 1-anthryl, 2-anthryl and 9-anthryl, preferably phenyl, 1-naphthyl and 2-naphthyl, particularly preferably phenyl,
- in IIa also hydrogen (H), in which case $R^1$=$R^2$ in the reaction product I.

The synthesis of the amines I can be referred to as a cyclizing alkylation.

The cyclizing alkylation of 1,4-aminobutanol can go through the intermediates

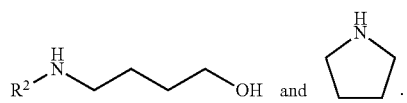

The cyclizing alkylation of 1,5-aminopentanol can go through the intermediates

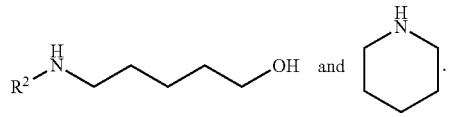

The cyclizing alkylation of aminodiglycol ($H_2N(CH_2)_2O(CH_2)_2OH$, ADG) can go through the intermediates

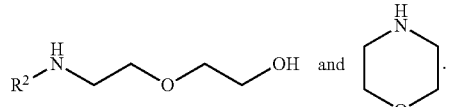

The cyclizing alkylation of aminoethylethanolamine of the formula IIa with $R^1$=H can go through the intermediates

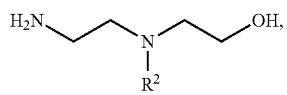
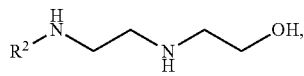
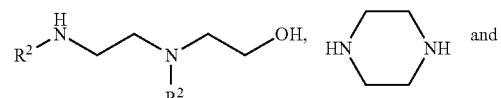
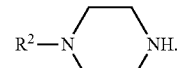

The cyclizing alkylation of aminoethylethanolamine of the formula IIa with $R^1$=$CH_3$ can go through the intermediates

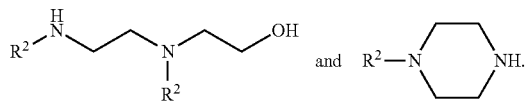

All pressures indicated are absolute pressures.

EXAMPLES

The following examples were carried out using a copper catalyst having the composition 55% by weight of CuO and 45% by weight of gamma-$Al_2O_3$ (after its last heat treatment and before reduction with hydrogen) (catalyst A).

The catalyst was produced by impregnating gamma-$Al_2O_3$ powder with an aqueous copper nitrate solution. Tableting was carried out by the usual method. Before commencement of the reaction, the catalyst was reduced in a stream of nitrogen at about 200° C. (see below).

Example 1

Preparation of N,N'-diethylpiperazine from aminoethylethanolamine and ethanol

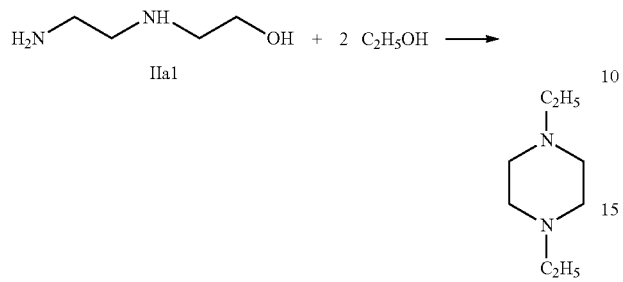

The reaction was carried out in a magnetically coupled 300 ml stirring autoclave with electric heating and cascade regulation of the internal temperature.

10.4 g of aminoethylethanolamine (IIa1) (0.1 mol), 92 g of ethanol (2 mol) and 10 g of a reduced and passivated catalyst A comprising copper on aluminum oxide (3×3 mm pellets) were introduced into the autoclave which had been made inert by means of nitrogen. The catalyst comprised, before reduction, 55% by weight of copper oxide (CuO) and 45% by weight of aluminum oxide. The reduction was carried out at from 180 to 200° C. and the passivation was carried out at <50° C. using air before the reaction. The reaction mixture was pressurized at room temperature with hydrogen up to a pressure of 10 bar. The autoclave was then heated to 200° C., further hydrogen was injected up to a total pressure of 80 bar and the reaction mixture was stirred (800 rpm) at 200° C. and 80 bar for 6 hours.

Gas-chromatographic analysis (GC column 30 m RTX 5 amine) indicated that the reaction output (without excess ethanol) at complete aminoethylethanolamine conversion comprised 74.4% by area of N,N'-diethylpiperazine.

It is known from example 2 in EP 257 443 A1 (see also the introductory part of the description above) that the primary amine n-pentylamine can be reacted with the primary alcohol n-pentanol in the presence of copper catalysts to form the tertiary amine tri-n-pentylamine. It would therefore have been expected that aminoethylethanolamine IIa1 would be converted entirely or at least partially into N,N'-diethylaminoethylethanolamine IVa with $R^1$=H and/or its ethylation product IVb with $R^1$=$C_2H_5$.

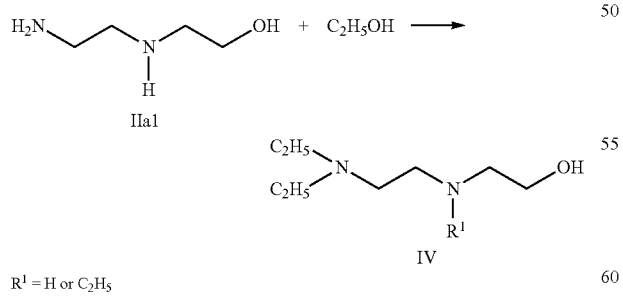

$R^1$ = H or $C_2H_5$

Both compounds IVa, IVb cannot undergo a cyclization to N,N'-diethylpiperazine. IVa and IVb were not detected by gas chromatography. This result and the high yields of N,N'-diethylpiperazine are therefore surprising to a person skilled in the art.

The same reasons for a surprising result apply to other starting compounds II, e.g. 1,4-aminobutanol, 1,5-aminopentanol and aminodiglycol (ADG).

The invention claimed is:

1. A process for preparing a cyclic tertiary amine of formula (I)

wherein:
A is a $C_4$-alkylene group, a $C_5$-alkylene group or a —$(CH_2)_2$—B—$(CH_2)_2$— group,
B is oxygen (O) or an N—$R^1$ radical,
$R^1$ is $C_1$-$C_5$-alkyl, aryl or $C_5$-$C_7$-cycloalkyl, and
$R^2$ is a $C_5$-$C_7$-cycloalkyl, $C_7$-$C_{20}$-aralkyl, or a linear or branched $C_2$-$C_{16}$-alkyl;
said process comprising:
(i) reacting an amino alcohol (II) from the group consisting of 1,4-aminobutanol, 1,5-aminopentanol, aminodiglycol (ADG) and aminoethylethanolamine of formula (IIa)

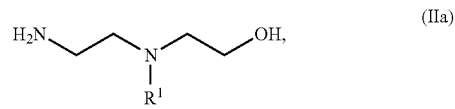

wherein:
$R^1$ of the aminoethylethanolamine of formula (IIa) is as defined above or hydrogen (H), wherein $R^1$ in the amine of the formula (I)=$R^2$ in the amine of the formula (I) when $R^1$ in the aminoethylethanolamine of formula (IIa) is H,
with a primary or secondary alcohol $R^2OH$ (III) at a temperature in the range of from 150 to 270° C. in the liquid phase in the presence of a copper-comprising heterogeneous catalyst comprising a catalytically active composition in a reactor.

2. The process according to claim 1, further comprising
(ii) separating off unreacted alcohol III or a homoazeotrope or heteroazeotrope of unreacted alcohol (III) and water from the reaction output of reaction step (i) by distillation in a first distillation unit and, when a homoazeotrope is present after azeotropic separation, recirculating the alcohol (III) to reaction step (i).

3. The process according to claim 2, further comprising
(iii) removing water of reaction from the bottom product from the first distillation unit by extraction with aqueous alkali metal hydroxide or alkaline earth metal hydroxide solution or by azeotropic distillation using a hydrocarbon in a second distillation unit; and
(iv) fractionally distilling the resulting output of (iii) to isolate tertiary amine (I).

4. The process according to claim 1, wherein the reaction of amino alcohol (II) with alcohol (III) is carried out continuously.

5. The process according to claim 2, wherein amino alcohol (II) and recirculated alcohol from step (ii) are fed in two separate streams or together into the reactor of reaction step (i).

6. The process according to claim 2, wherein recirculated alcohol from step (ii) and the amino alcohol (II) are preheated individually or as a mixture to a temperature in the range from 20 to 240° C. before introduction into the reactor of reaction step (i).

7. The process according to claim 1, wherein the cyclic tertiary amine produced is N-alkylpyrrolidine and the amino alcohol (II) is 1,4-aminobutanol.

8. The process according to claim 1 wherein the cyclic tertiary amine produced is N-alkylpiperidine and the amino alcohol (II) is 1,5-aminopentanol.

9. The process according to claim 1 wherein the cyclic tertiary amine produced is N-alkylmorpholine and the amino alcohol (II) is aminodiglycol.

10. The process according to claim 1 wherein the cyclic tertiary amine produced is N,N'-dialkylpiperazine of formula (V)

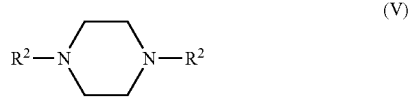

(V)

and the amino alcohol (II) is aminoethylethanolamine of formula (IIa)

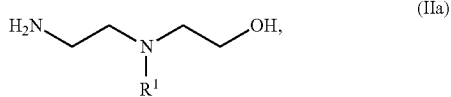

(IIa)

wherein R¹ is hydrogen.

11. The process according to claim 1 wherein the cyclic tertiary amine produced is N,N'-dialkylpiperazine of formula (VI)

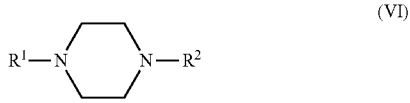

(VI)

and the amino alcohol II is aminoethylethanolamine of formula (IIa)

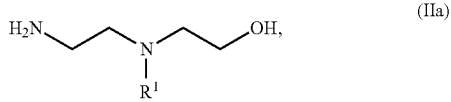

(IIa)

where R¹ is not hydrogen.

12. The process according to claim 1, wherein the reaction is carried out in the presence of a catalyst comprising copper oxide and aluminum oxide.

13. The process according to claim 1, wherein the catalytically active composition of the catalyst before reduction with hydrogen comprises from 25 to 80% by weight of $Al_2O_3$, from 20 to 75% by weight of oxygen-comprising compounds of copper, calculated as CuO, from 0 to 2% by weight of oxygen-comprising compounds of sodium, calculated as $Na_2O$, and less than 5% by weight of oxygen-comprising compounds of nickel, calculated as NiO.

14. The process according to claim 1, wherein the catalytically active composition of the catalyst before reduction with hydrogen comprises less than 1% by weight of oxygen-comprising compounds of nickel, calculated as NiO.

15. The process according to claim 1, wherein the catalytically active composition of the catalyst before reduction with hydrogen comprises less than 1% by weight of oxygen-comprising compounds of cobalt, calculated as CoO.

16. The process according to claim 1, wherein the catalytically active composition of the catalyst before reduction with hydrogen comprises from 30 to 70% by weight of $Al_2O_3$ and from 30 to 70% by weight of oxygen-comprising compounds of copper, calculated as CuO.

17. The process according to claim 1, wherein the catalytically active composition of the catalyst before reduction with hydrogen comprises from 0.05 to 1% by weight of oxygen-comprising compounds of sodium, calculated as $Na_2O$.

18. The process according to claim 1, wherein the catalytically active composition of the catalyst does not comprise any nickel, cobalt and/or ruthenium.

19. The process according to claim 1, wherein the reaction is carried out isothermally with a temperature deviation of not more than +/−8° C.

20. The process according to claim 1, wherein $H_2$ is fed into the reactor in reaction step (i).

21. The process according to claim 4, wherein the reaction in step (i) is carried out in a tube reactor.

22. The process according to claim 4, wherein the reaction in step (i) is carried out in a shell-and-tube reactor or in a monostream plant.

23. The process according to claim 1, wherein the reaction in step (i) is carried out at an absolute pressure in the range from 50 to 150 bar.

24. The process according to claim 1, wherein the alcohol (III) is used in step (i) in a 1- to 25-fold molar amount based on the amino alcohol (II) used.

25. The process according to claim 1, wherein the catalyst is arranged as a fixed bed in the reactor.

* * * * *